(12) United States Patent
Walsh et al.

(10) Patent No.: US 7,387,883 B2
(45) Date of Patent: *Jun. 17, 2008

(54) METHODS FOR DETECTING BACTERIAL PATHOGENS

(75) Inventors: John D. Walsh, Durham, NC (US); Jones M. Hyman, Wake Forest, NC (US)

(73) Assignee: bioMerieux, Inc, Durham, NC (US)

( * ) Notice: Subject to any disclaimer, the term of this patent is extended or adjusted under 35 U.S.C. 154(b) by 165 days.

This patent is subject to a terminal disclaimer.

(21) Appl. No.: 11/005,668

(22) Filed: Dec. 7, 2004

(65) Prior Publication Data

US 2005/0124026 A1  Jun. 9, 2005

Related U.S. Application Data

(60) Provisional application No. 60/572,997, filed on May 20, 2004, provisional application No. 60/527,925, filed on Dec. 9, 2003.

(51) Int. Cl.
C12Q 1/14 (2006.01)
C14Q 1/04 (2006.01)

(52) U.S. Cl. .......................................... 435/36; 435/34
(58) Field of Classification Search .................. 435/36
See application file for complete search history.

(56) References Cited

U.S. PATENT DOCUMENTS

| | | | | |
|---|---|---|---|---|
| 4,164,449 | A * | 8/1979 | Dorn et al. ...................... | 435/30 |
| 4,362,531 | A * | 12/1982 | de Steenwinkel et al. .. | 436/512 |
| 4,617,264 | A * | 10/1986 | Whiteley et al. ........... | 435/7.36 |
| 4,632,902 | A | 12/1986 | Waters et al. | |
| 4,665,024 | A * | 5/1987 | Mansour ....................... | 435/34 |
| 5,496,706 | A | 3/1996 | Kuusela et al. | |
| 5,989,821 | A | 11/1999 | Goh et al. | |
| 6,022,682 | A * | 2/2000 | Mach et al. ..................... | 435/4 |
| 6,156,507 | A | 12/2000 | Hiramatsu et al. | |
| 6,277,570 | B1 * | 8/2001 | Wood et al. ..................... | 435/6 |
| 6,312,903 | B1 | 11/2001 | Jannes et al. | |
| 6,340,571 | B1 | 1/2002 | Merlin et al. | |
| 6,936,259 | B2 * | 8/2005 | Potter et al. .............. | 424/244.1 |
| 2001/0044125 | A1 * | 11/2001 | Ono et al. .................. | 435/7.32 |
| 2002/0055101 | A1 | 5/2002 | Bergeron et al. | |
| 2002/0086289 | A1 | 7/2002 | Straus | |
| 2002/0147317 | A1 | 10/2002 | Bentsen et al. | |
| 2003/0054436 | A1 | 3/2003 | Kunsch et al. | |

FOREIGN PATENT DOCUMENTS

| | | |
|---|---|---|
| EP | 0323331 | 7/1989 |
| WO | WO 98/32874 | 7/1998 |
| WO | WO 02/079486 | 10/2002 |
| WO | WO 02/082086 | 10/2002 |

OTHER PUBLICATIONS

Brown DFJ et al (2001) Evaluation of Mastalex latex agglutination test for methicillin resistance in *Staphylococcus aureus* grown on different screening media. J Antimicrob Chemother, vol. 47, pp. 187-189.*

Simonson et al (Dec. 1986) Rapid serological identification of *Vibrio vulnificus* by anti-H coagglutination. Appl Environ Microbiol, vol. 52, No. 6, pp. 1299-1304.*

Anonymous, "*Slidex Staph-Kit*" Internet Article, 'Online, Retrieved from Internet: URL:http://www.biomerieux-usa.com/clinical/microbiology/slidex/slidex_staph.htm.

Anonymous, "*Pastorex Staph Plus Tes*", Technical Manual, 'Online (Jul. 31, 2000), Retrieved from Internet: URL:http://microbiology.mtsinai.on.ca/manual/tech/tech32.pdf.

Van Griethuysen Arjanne et al., "*International Multicenter Evaluation Of Latex Agglutination Tests For Identification Of Staphylococcus aureus*", Journal of Clinical Microbiology, vol. 32, No. 1, pp. 86-89 (Jan. 2001).

Speers et al., "*Evaluation Of Four Methods For Rapid Identification Of Staphylococcus aureus From Blood Cultures*", Journal of Clinical Microbiology, vol. 23, No. 4, (Apr. 1998).

* cited by examiner

Primary Examiner—Herbert J Lilling

(57) ABSTRACT

The present invention provides for methods for detecting *Staphylococcus aureus* in a sample. A preferred method includes the steps of: mixing a sample comprising a medium and microorganisms with a first solution in a vessel, the microorganisms suspected of comprising *Staphylococcus aureus*; separating the microorganisms from the medium and the bulk of the first solution and removing the medium and the bulk of the first solution from the vessel; adding a second solution to the vessel to resuspend the microorganisms; and detecting *Staphylococcus aureus* in the resulting suspension of step (c) by using an agglutination test.

13 Claims, No Drawings

METHODS FOR DETECTING BACTERIAL PATHOGENS

CROSS-REFERENCE TO RELATED APPLICATIONS

This application claims the benefit of U.S. Provisional Patent Application No. 60/527,925 filed on Dec. 9, 2003 and U.S. Provisional Patent Application No. 60/572,997 filed on May 20, 2004.

FIELD OF THE INVENTION

The present invention relates to methods for the identification of bacterial pathogens including *Staphylococci*. More particularly, the present invention relates to the identification of *Staphylococcus aureus* in samples.

BACKGROUND OF THE INVENTION

The genus *Staphylococcus* includes at least 20 distinct species. (For a review, see Novick, R. P., The *Staphylococcus* as a Molecular Genetic System, Chapter 1, pgs. 1-37 in MOLECULAR BIOLOGY OF THE *STAPHYLOCOCCI*, R. Novick, Ed., VCH Publishers, New York (1990)). The species differ from one another by 80% or more, by hybridization kinetics, whereas strains within a species are at least 90% identical by the same measure.

The species *Staphylococcus aureus* is a gram-positive, facultatively aerobic, clump-forming cocci considered among the most virulent species of the genus.

*Staphylococcus aureus* is a ubiquitous pathogen. (See, for instance, Mims et al., MEDICAL MICROBIOLOGY, Mosby-Year Book Europe Limited, London, UK (1993)). It is an etiological agent of a variety of conditions, ranging in severity from mild to fatal. A few of the more common conditions caused by *S. aureus* infection are burns, cellulitis, eyelid infections, food poisoning, joint infections, neonatal conjunctivitis, osteomyelitis, skin infections, surgical wound infection, scalded skin syndrome and toxic shock syndrome. *Staphylococcus aureus* also causes more serious illnesses such as pneumonia, meningitis and bacteremia.

When introduced in food, *Staphylococcus aureus* may produce one or more *Staphylococcal* enterotoxins. If ingested, heat stable *Staphylococcal* enterotoxins may produce symptoms of food poisoning and a range of other diseases.

*Staphylococcus aureus* possesses a protective cell wall which comprises a cross-linked peptidoglycan layer. The cell wall is resistant to phagocytosis which is thought to be due, in part, to the production of Protein A on the cell surface. *Staphylococcus aureus* also produces hemolytic toxin which may damage blood cells and immune cells.

Accordingly, it is readily apparent that it is important that bacterial pathogens such as *Staphylococcus aureus* can be identified in samples and that such pathogens be identified as quickly as possible so that patients can be treated quickly. To that end, several methods have been disclosed for detecting *Staphylococcus aureus*. For example, U.S. Pat. No. 5,496,706 discloses a method for detecting *Staphylococcus aureus* in a sample. The method uses anti-MRSA-230 antibodies to detect *Staphylococcus aureus* by visible agglutination means. This method, though, can be quite expensive.

Many laboratories perform a slide coagulase test as a rapid, inexpensive method for presumptive identification of *S. aureus*. This test relies on the observation of clumping of a heavy suspension of *S. aureus* cells in the presence of a drop of plasma placed on a slide. The clumping is mediated by the binding of fibrinogen with a specific receptor of the surface of the bacterium, termed clumping factor. However, a slide coagulase test has significant drawbacks. For example, 10 to 15% of *S. aureus* isolates yield false negative results requiring all negatives to be confirmed in a tube coagulase test. A tube coagulase test is another commonly used method for identifying *S. aureus*. This method, though, requires an incubation period of 4 to 24 hours.

In addition, rapid cycle, real-time PCR methods can provide results in thirty (30) minutes and in situ probe hybridization methods such as FISH can provide results within ninety (90) minutes. However, these methods are expensive and/or labor intensive.

Further, direct testing of positive blood culture bottles using latex tests has not been recommended due to poor assay sensitivity and specificity. See Spears, D. J. et al., J. Clin. Microbiol. 36:1032-1034 (1998) and Slidex Staph Plus, 09760 C-GB, bioMerieux, Inc. (2000). Thus, there is a need in the art for a rapid, accurate and inexpensive means for detecting and identifying *Staphylococcus aureus*.

SUMMARY OF THE INVENTION

The present invention provides for a method for detecting *Staphylococcus aureus* in a sample which is rapid, accurate and less expensive than the methods of the prior art. The method comprises the steps of:
  (a) mixing a sample comprising a medium and microorganisms with a first solution in a vessel, the microorganisms suspected of comprising *Staphylococcus aureus*;
  (b) separating the microorganisms from the medium and the bulk of the first solution and removing the medium and the bulk of the first solution from the vessel;
  (c) adding a second solution to the vessel to resuspend the microorganisms; and
  (d) detecting the presence of *Staphylococcus aureus* in the resulting suspension of step (c) by using an agglutination test.

The present invention also provides for another method for detecting *Staphylococcus aureus* in a sample. This method comprises the steps of:
  (a) preparing a sample comprising a medium, microorganisms and plasma, serum, blood or a blood component, the microorganisms suspected of comprising *Staphylococcus aureus*;
  (b) mixing the sample with a first solution in a vessel;
  (c) separating the microorganisms from the medium, the bulk of the first solution and the bulk of the plasma, serum, blood or blood component and removing the medium, the bulk of the first solution and the bulk of the plasma, serum, blood or blood component from the vessel;
  (d) adding a second solution to the vessel to resuspend the microorganisms; and
  (e) detecting the presence of *Staphylococcus aureus* in the resulting suspension of step (d) by using an agglutination test.

The above-described methods provide a definitive result within fifteen (15) minutes allowing the attending physician to be notified of the identification of this important pathogen.

Furthermore, modifications of these methods may be used to assess the presence of other pathogenic bacteria which may express the same or similar virulence factors to *S. aureus*.

DETAILED DESCRIPTION OF THE INVENTION

As stated above, the present invention provides for a method for detecting *Staphylococcus aureus* in a sample comprising the steps of:
(a) mixing a sample comprising a medium and microorganisms with a first solution in a vessel, the microorganisms suspected of comprising *Staphylococcus aureus*;
(b) separating the microorganisms from the medium and the bulk of the first solution and removing the medium and the bulk of the first solution from the vessel;
(c) adding a second solution to the vessel to resuspend the microorganisms; and
(d) detecting the presence of *Staphylococcus aureus* in the resulting suspension of step (c) by using an agglutination test.

Samples that can be used in this method of the present invention can be obtained from any source including, but not limited to, blood, blood products, tissue, ascites, culture media, body fluids, skin, pus, uro-genital specimens, feces, foodstuffs, beverages, cosmetic products, pharmaceutical products, healthcare products, surfaces such as floors and tables, and airborne particles such as pollen and dust. The sample will be one that is suspected of having microorganisms, in particular, *Staphylococcus aureus*. The sample may already have been tested for the presence of microorganisms and have tested positive for microorganisms. The sample may require the addition of a medium prior to step (a). The amount of medium to be added, if necessary, would be dependent upon the estimated number of microorganisms in the sample and could easily be ascertained by one skilled in the art.

Plasma, serum, blood or a blood component is preferably mixed with the sample and the first solution in step (a). If plasma, serum, blood or a blood component is mixed with the sample and the first solution, the bulk of the plasma, serum, blood or a blood component is separated along with the medium and the bulk of the first solution from the microorganisms and removed from the vessel during step (b). The sample, though, may be obtained from a source such as blood, blood products, tissue, body fluids, skin, pus, etc., and therefore already include plasma, serum, blood or a blood component. In such instances, the bulk of the plasma, serum, blood or a blood component is separated along with the medium and the bulk of the first solution from the microorganisms and removed from the vessel during step (b).

Step (a) provides that the sample and the first solution are mixed in a vessel and this can be accomplished by briefly vortexing the vessel. The vessel is preferably a conical tube.

The amount of sample that can be mixed with the first solution in step (a) is from about 0.1 to about 10 mL. Preferably, the amount of sample mixed with the first solution in step (a) is about 5.0 mL.

The amount of the first solution that can be mixed with the sample in step (a) is from about 0.1 to about 10 mL. The first solution preferably comprises an alkaline reagent. Alkaline reagents that can be used with the present invention include, but are not limited to, ethanolamine, tri-sodium phosphate, sodium hydroxide and potassium hydroxide. The first solution can also comprise a detergent. Most preferably, the first solution comprises an alkaline reagent, a detergent and a chelating agent. Detergents that can be used with the present invention include, but are not limited to, cholic acid, Triton X-100, deoxycholic acid, cetrimide, N-Dodecylsulfobetaine, digitonin, n-dodecyl-.beta.-D-maltoside, glycodeoxycholic acid, n-lauroylsarcosine, lauryl sulfate, saponin, polyoxyethylene sorbitan monooleate, polyethylene glycol P-1, 1,3,3-tetramethylbutylphenyl ether and polyoxyethylene derivatives of fatty acids. Chelating agents that can be used with the present invention include, but are not limited to, EGTA and EDTA.

In a preferred embodiment, the first solution comprises sodium hydroxide, Triton X-100 and EDTA. More particularly, the first solution comprises 0.2 N sodium hydroxide, 1.0% Triton X-100 and 1 mM EDTA. The amount of this first solution that can be mixed with the sample in step (a) is from about 0.1 to about 10 mL. Preferably, the amount of this first solution mixed with the sample in step (a) is about 5.0 mL.

In another preferred embodiment, the first solution comprises an acidic solution having a pH in the range of from about 2.5 to about 5.5. Preferably, the acidic solution comprises acetate or citrate. Further, the acidic solution preferably comprises one or more of the following: a detergent, a salt, a chelating agent and an alcohol. Any of the aforementioned detergents and chelating agents can be used although it is preferred that the acidic solution include one of the detergents cetrimide or N-Dodecylsulfobetaine.

The above method provides for separating the microorganisms from the medium and the bulk of the first solution and removing the medium and the bulk of the first solution from the vessel. Preferably, the microorganisms can be separated from the medium and the bulk of the first solution by centrifugation or filtration. Most preferably, the microorganisms are separated from the medium and the bulk of the first solution by centrifugation for ten (10) minutes at $\geq 1,000$ G to pellet the microorganisms. Preferably, the medium is a growth medium.

Step (c) of the above method provides for adding a second solution to the vessel to resuspend the microorganisms. After the second solution is added to the vessel, the vessel should be vortexed.

The amount of the second solution that can be added to the vessel in step (c) is from about 0.05 mL to about 5 mL. Preferably, the second solution comprises an acidic solution and/or a buffer such as Tris, HEPES, MOPS and phosphate. Buffers that can be used with the present invention have a pKa in the range of from about 5.0 to about 9.0. More preferably, buffers that can be used with the present invention have a pKa in the range of from about 6.0 to about 8.0.

Preferably, the second solution comprises a detergent and/or a salt. Detergents that can be used with the present invention include, but are not limited to, cholic acid, deoxycholic acid, cetrimide, N-Dodecylsulfobetaine, digitonin, n-dodecyl-.beta.-D-maltoside, glycodeoxycholic acid, n-lauroylsarcosine, lauryl sulfate, saponin, polyoxyethylene sorbitan monooleate, polyethylene glycol P-1,1,3,3-tetramethylbutylphenyl ether, polyoxyethylene derivatives of fatty acids and Triton X-100. Salts that can be used with present invention include, but are not limited to, potassium chloride, sodium chloride, magnesium chloride, magnesium sulfate and calcium chloride.

In a preferred embodiment, the second solution comprises Tris, sodium chloride and Tween 80. More particularly, the second solution comprises 0.1 M Tris (pH 7.2), 0.15 M sodium chloride and 0.5% Tween 80. The amount of this second solution that can be added to the vessel in step (c) is from about 0.05 mL to about 5 mL. Preferably, the amount of this second solution added to the vessel in step (c) is from about 0.5 to about 1.0 mL.

Step (d) of the above method provides for detecting the presence of *Staphylococcus aureus* in the resulting suspension in step (c). This is preferably accomplished by using an agglutination test such as the Slidex Staph Plus test. Preferably, 20 to 40 µL of the resulting suspension from step (c) is added to one drop of the control and then tested using a Slidex Staph Plus test. Alternatively, a Staphytect Plus test from Oxoid could be used.

The present invention also provides for another method for detecting *Staphylococcus aureus* in a sample. This method comprises the steps of:
(a) preparing a sample comprising a medium, microorganisms and plasma, serum, blood or a blood component, the microorganisms suspected of comprising *Staphylococcus aureus*;
(b) mixing the sample with a first solution in a vessel;
(c) separating the microorganisms from the medium, the bulk of the first solution and the bulk of the plasma, serum, blood or blood component and removing the medium, the bulk of the first solution and the bulk of the plasma, serum, blood or blood component from the vessel;
(d) adding a second solution to the vessel to resuspend the microorganisms; and
(e) detecting the presence of *Staphylococcus aureus* in the resulting suspension of step (d) by using an agglutination test.

Step (a) provides for preparing a sample comprising a medium, microorganisms and plasma, serum, blood or a blood component. The type of sample to be tested will determine how the sample will be prepared. Samples that can be used in the methods of the present invention can be obtained from any source including, but not limited to, blood, blood products, tissue, ascites, culture media, body fluids, skin, pus, uro-genital specimens, feces, foodstuffs, beverages, cosmetic products, pharmaceutical products, healthcare products, surfaces such as floors and tables, and airborne particles such as pollen and dust. The sample will be one that is suspected of having microorganisms, in particular, *Staphylococcus aureus*. The sample may already have been tested for the presence of microorganisms and have tested positive for microorganisms. The sample may require the addition of a medium and/or the sample may require the addition of plasma, serum, blood or a blood component. The amount of medium and/or plasma, serum, blood or blood component to be added, if necessary, would be dependent upon the estimated number of microorganisms in the sample and could easily be ascertained by one skilled in the art.

Step (b) provides that the sample and the first solution are mixed in a vessel and this can be accomplished by briefly vortexing the vessel. The vessel is preferably a conical tube.

The amount of sample that can be mixed with the first solution in step (b) is from about 0.1 to about 10 mL. Preferably, the amount of sample mixed with the first solution in step (b) is about 5.0 mL.

The amount of the first solution that can be mixed with the sample in step (b) is from about 0.1 to about 10 mL. The first solution preferably comprises an alkaline reagent. Alkaline reagents that can be used with the present invention include, but are not limited to, ethanolamine, tri-sodium phosphate, sodium hydroxide and potassium hydroxide. The first solution can also comprise a detergent. Most preferably, the first solution comprises an alkaline reagent, a detergent and a chelating agent. Detergents that can be used with the present invention include, but are not limited to, cholic acid, Triton X-100, deoxycholic acid, cetrimide, N-Dodecylsulfobetaine, digitonin, n-dodecyl-.beta.-D-maltoside, glycodeoxycholic acid, n-lauroylsarcosine, lauryl sulfate, saponin, polyoxyethylene sorbitan monooleate, polyethylene glycol P-1, 1,3,3-tetramethylbutylphenyl ether and polyoxyethylene derivatives of fatty acids. Chelating agents that can be used with the present invention include, but are not limited to, EGTA and EDTA.

In a preferred embodiment, the first solution comprises sodium hydroxide, Triton X-100 and EDTA. More particularly, the first solution comprises 0.2 N sodium hydroxide, 1.0% Triton X-100 and 1 mM EDTA. The amount of this first solution that can be mixed with the sample in step (b) is from about 0.1 to about 10 mL. Preferably, the amount of this first solution mixed with the sample in step (b) is about 5.0 mL.

In another preferred embodiment, the first solution comprises an acidic solution having a pH in the range of from about 2.5 to about 5.5. Preferably, the acidic solution comprises acetate or citrate. Further, the acidic solution preferably comprises one or more of the following: a detergent, a salt, a chelating agent and an alcohol. Any of the aforementioned detergents and chelating agents can be used although it is preferred that the acidic solution include one of the detergents cetrimide or N-Dodecylsulfobetaine.

The above method provides for separating the microorganisms from the medium, the bulk of the first solution and the bulk of the plasma, serum, blood or blood component and removing the medium, the bulk of the first solution and the bulk of the plasma, serum, blood or blood component from the vessel. Preferably, the microorganisms can be separated from the medium, the bulk of the first solution and the bulk of the plasma, serum, blood or blood component by centrifugation or filtration. Most preferably, the microorganisms are separated from the medium, the bulk of the first solution and the bulk of the plasma, serum, blood or blood component by centrifugation for ten (10) minutes at $\geq 1,000$ G to pellet the microorganisms. Preferably, the medium is a growth medium.

Step (d) of the above method provides for adding a second solution to the vessel to resuspend the microorganisms. After the second solution is added to the vessel, the vessel should be vortexed.

The amount of the second solution that can be added to the vessel in step (d) is from about 0.05 mL to about 5 mL. Preferably, the second solution comprises an acidic solution and/or a buffer such as Tris, HEPES, MOPS and phosphate. Buffers that can be used with the present invention have a pKa in the range of from about 5.0 to about 9.0. More preferably, buffers that can be used with the present invention have a pKa in the range of from about 6.0 to about 8.0.

Preferably, the second solution comprises a detergent and/or a salt. Detergents that can be used with the present invention include, but are not limited to, cholic acid, deoxycholic acid, cetrimide, N-Dodecylsulfobetaine, digitonin, n-dodecyl-.beta.-D-maltoside, glycodeoxycholic acid, n-lauroylsarcosine, lauryl sulfate, saponin, polyoxyethylene sorbitan monooleate, polyethylene glycol P-1,1,3,3-tetramethylbutylphenyl ether, polyoxyethylene derivatives of fatty acids and Triton X-100. Salts that can be used with present invention include, but are not limited to, potassium chloride, sodium chloride, magnesium chloride, magnesium sulfate and calcium chloride.

In a preferred embodiment, the second solution comprises Tris, sodium chloride and Tween 80. More particularly, the second solution comprises 0.1 M Tris (pH 7.2), 0.15 M sodium chloride and 0.5% Tween 80. The amount of this second solution that can be added to the vessel in step (d) is from about 0.05 mL to about 5 mL. Preferably, the amount of this second solution added to the vessel in step (d) is from about 0.5 to about 1.0 mL.

Step (e) of the above method provides for detecting the presence of *Staphylococcus aureus* in the resulting suspension in step (d). This is preferably accomplished by using an agglutination test such as the Slidex Staph Plus test. Preferably, 20 to 40 μL of the resulting suspension from step (d) is added to one drop of the control and then tested using a Slidex Staph Plus test. Alternatively, a Staphytect Plus test from Oxoid could be used.

The present invention also provides for another method for detecting *Staphylococcus aureus* in a sample. This method comprises the steps of:

(a) mixing a sample comprising a medium, an adsorbent and microorganisms with a first solution in a vessel, the microorganisms suspected of comprising *Staphylococcus aureus*;

(b) separating the adsorbent and microorganisms from the medium and the bulk of the first solution and removing the medium and the bulk of the first solution from the vessel;

(c) adding a second solution to the vessel to resuspend the adsorbent and the microorganisms; and (d) detecting *Staphylococcus aureus* in the resulting suspension in step (c) using an agglutination test.

Samples that can be used in this method of the present invention can be obtained from any source including, but not limited to, blood, blood products, tissue, ascites, culture media, body fluids, skin, pus, uro-genital specimens, feces, foodstuffs, beverages, cosmetic products, pharmaceutical products, healthcare products, surfaces such as floors and tables, and airborne particles such as pollen and dust. The sample will be one that is suspected of having microorganisms, in particular, *Staphylococcus aureus*. The sample may already have been tested for the presence of microorganisms and have tested positive for microorganisms. The sample may require the addition of a medium prior to step (a) and/or the sample may require the addition of an adsorbent prior to step (a). The amount of medium and/or adsorbent to be added, if necessary, would be dependent upon the estimated number of microorganisms in the sample and could easily be ascertained by one skilled in the art.

Plasma, serum, blood or a blood component is preferably mixed with the sample and the first solution in step (a). If plasma, serum, blood or a blood component is mixed with the sample and the first solution, the bulk of the plasma, serum, blood or a blood component is separated along with the medium and the bulk of the first solution from the microorganisms and removed from the vessel during step (b). The sample, though, may be obtained from a source such as blood, blood products, tissue, body fluids, skin, pus, etc., and therefore already include plasma, serum, blood or a blood component. In such instances, the bulk of the plasma, serum, blood or a blood component is separated along with the medium and the bulk of the first solution from the microorganisms and removed from the vessel during step (b).

Step (a) provides that the sample and first solution are mixed in a vessel and this can be accomplished by briefly vortexing the vessel. The vessel is preferably a conical tube.

The adsorbent is selected from the group consisting of aluminum oxide, colloidal native hydrated aluminum silicates, crystalline hydrated alkali-aluminum silicates, silica, siliceous frustules, fragments of various species of diatoms, amorphous carbon, ion exchange resins, polymeric resin adsorbents and polystyrene resin cross-linked with divinyl benzene.

The amount of sample that can be mixed with the first solution in step (a) is about 0.1 mL to about 10 mL. Preferably, the amount of sample mixed with the first solution in step (a) is about 5.0 mL.

The amount of the first solution that can be mixed with the sample in step (a) is from about 0.1 to about 10 mL. The first solution preferably comprises an alkaline reagent. Alkaline reagents that can be used include, but are not limited to, ethanolamine, tri-sodium phosphate, sodium hydroxide and potassium hydroxide. The first solution can also comprise a detergent. Most preferably, the first solution comprises an alkaline reagent, a detergent and a chelating agent. Detergents that can be used with the present invention include, but are not limited to, cholic acid, deoxycholic acid, cetrimide, N-Dodecylsulfobetaine, digitonin, n-dodecyl-.beta.-D-maltoside, glycodeoxycholic acid, n-lauroylsarcosine, lauryl sulfate, saponin, polyoxyethylene sorbitan monooleate, polyethylene glycol P-1,1,3,3-tetramethylbutylphenyl ether, Triton X-100 and polyoxyethylene derivatives of fatty acids. Chelating agents that can be used with the present invention include, but are not limited to, EGTA and EDTA.

In a preferred embodiment, the first solution comprises sodium hydroxide, Triton X-100 and EDTA. More particularly, the first solution comprises 0.2 N sodium hydroxide, 1.0% Triton X-100 and I mM EDTA. The amount of this first solution that can be mixed with the sample in step (a) is from about 0.1 to about 10 mL. Preferably, the amount of this first solution mixed with the sample in step (a) is about 5.0 mL.

In another preferred embodiment, the first solution comprises an acidic solution having a pH in the range of from about 2.5 to about 5.5. Preferably, the acidic solution comprises acetate or citrate. Further, the acidic solution preferably comprises one or more of the following: a detergent, a salt, a chelating agent and an alcohol. Any of the aforementioned detergents and chelating agents can be used although it is preferred that the acidic solution include one of the detergents cetrimide or N-Dodecylsulfobetaine.

The above method provides for separating the adsorbent and the microorganisms from the medium and the bulk of the first solution and removing the medium and the bulk of the first solution from the vessel. Preferably, the adsorbent and the microorganisms can be separated from the medium and the bulk of the first solution by centrifugation or filtration. Most preferably, the adsorbent and the microorganisms are separated from the medium and the bulk of the first solution by centrifugation for ten (10) minutes at ≧1,000 G to pellet the adsorbent and the microorganisms. Preferably, the medium is a growth medium.

Step (c) of the above method provides for adding a second solution to the vessel to resuspend the adsorbent and the microorganisms. After the second solution is added to the vessel, the vessel should be vortexed.

The amount of the second solution that can be added to the vessel in step (c) is from about 0.05 mL to about 5 mL. Preferably, the second solution comprises an acidic solution and/or a buffer such as Tris, HEPES, MOPS and phosphate. Buffers that can be used with the present invention have a pKa in the range of from about 5.0 to about 9.0. More preferably, buffers that can be used with the present invention have a pKa in the range of from about 6.0 to about 8.0.

Preferably, the second solution comprises a detergent and/or a salt. Detergents that can be used with the present invention include, but are not limited to, cholic acid, deoxycholic acid, cetrimide, N-Dodecylsulfobetaine, digitonin, n-dodecyl-.beta.-D-maltoside, glycodeoxycholic acid, n-lauroylsarcosine, lauryl sulfate, Triton X-100, saponin, polyoxyethylene sorbitan monooleate, polyethylene glycol P-1,1,3,3-tetramethylbutylphenyl ether and polyoxyethylene derivatives of fatty acids. Salts that can be used with present invention include, but are not limited to, potassium chloride, sodium chloride, magnesium chloride, magnesium sulfate and calcium chloride.

In a preferred embodiment, the second solution comprises Tris, sodium chloride and Tween 80. More particularly, the second solution comprises 0.1 M Tris (pH 7.2), 0.15 M sodium chloride and 0.5% Tween 80. The amount of this second solution that can be added to the vessel in step (c) is from about 0.05 to about 5 mL. Preferably, the amount of this second solution added to the vessel in step (c) is from about 0.5 to about 1.0 mL.

Step (d) of the above method provides for detecting the presence of *Staphylococcus aureus* in the resulting suspension in step (c). This is preferably accomplished by using a latex test such as the Slidex Staph Plus test. Preferably, 20 to 40 μL of the resulting suspension from step (c) is added to one drop of the control and then tested using a Slidex Staph Plus test. Alternatively, a Staphytect Plus test from Oxoid could be used.

Another embodiment of the present invention provides for detecting *Staphylococcus aureus* in a sample by:
  (a) preparing a sample comprising a medium and microorganisms, the microorganisms suspected of comprising *Staphylococcus aureus*;
  (b) mixing the sample with a first solution in a vessel;
  (c) separating the microorganisms from the medium and a bulk of the first solution and removing the medium and the bulk of the first solution from the vessel;
  (d) adding a second solution to the vessel to resuspend the microorganisms; and
  (e) detecting the presence of *Staphylococcus aureus* in the resulting suspension of step (d) by using an agglutination test.

In this embodiment, plasma, serum, blood or a blood component can be added to the sample in step (a) and separated and removed from the vessel in step (c) along with the medium and the bulk of the first solution.

Step (a) provides for preparing a sample comprising a medium and microorganisms. The type of sample to be tested will determine how the sample will be prepared. The samples used in this method and any of the methods for detecting *S. aureus* according to the present invention can be obtained from any source including, but not limited to, blood, blood products, tissue, ascites, culture media, body fluids, skin, pus, uro-genital specimens and feces. Samples may also be obtained for detection from foodstuffs and beverages; from cosmetic, pharmaceutical and healthcare products; from surfaces such as floors, tables, and the like; and from airborne particles, such as pollen and dust. The sample will be one that is suspected of having microorganisms, in particular, *Staphylococcus aureus*. The sample may already have been tested for the presence of microorganisms and have tested positive for microorganisms. The sample to be prepared during step (a) includes medium. If the sample does not have any medium, medium will need to be added to the sample during step (a). The amount of medium to add to the sample during step (a), if necessary, will be dependent upon the estimated number of microorganisms in the sample and this should be easily ascertainable by one skilled in the art.

Step (b) of this embodiment provides that the sample and first solution are mixed in a vessel and this can be accomplished by briefly vortexing the vessel. The vessel is preferably a conical tube. The amount of sample that can be mixed with the first solution in step (b) is about 0.1 mL to about 10 mL. Preferably, the amount of sample mixed with the first solution in step (b) is about 5.0 mL. The amount of the first solution that can be mixed with the sample in step (b) is from about 0.1 to about 10 mL. The first solution preferably comprises an alkaline reagent. Alkaline reagents that can be used include, but are not limited to, ethanolamine, tri-sodium phosphate, sodium hydroxide and potassium hydroxide. The first solution can also comprise a detergent. Most preferably, the first solution comprises an alkaline reagent, a detergent and a chelating agent. Any of the aforementioned detergents and chelating agents can be used.

It is preferred in this embodiment that the first solution comprise sodium hydroxide, Triton X-100 and EDTA. More particularly, the first solution comprises 0.2 N sodium hydroxide, 1.0% Triton X-100 and 1 mM EDTA. The amount of this first solution that can be mixed with the sample in step (b) is from about 0.1 to about 10 mL. Preferably, the amount of this first solution mixed with the sample in step (b) is about 5.0 mL.

Alternatively, the first solution can comprise an acidic solution having a pH in the range of from about 2.5 to about 5.5. Preferably, the acidic solution comprises acetate or citrate. Further, the acidic solution preferably comprises one or more of the following: a detergent, a salt, a chelating agent and an alcohol. Any of the aforementioned detergents and chelating agents can be used although it is preferred that the acidic solution include one of the detergents cetrimide or N-Dodecylsulfobetaine.

This method provides for separating the microorganisms from the medium and the bulk of the first solution and removing the medium and the bulk of the first solution from the vessel. Preferably, the microorganisms can be separated from the medium and the bulk of the first solution by centrifugation or filtration. Most preferably, the microorganisms are separated from the medium and the bulk of the first solution by centrifugation for ten (10) minutes at $\geq 1,000$ G to pellet the microorganisms.

Step (d) of this method provides for adding a second solution to the vessel to resuspend the microorganisms. After the second solution is added to the vessel, the vessel should be vortexed. The amount of the second solution that can be added to the vessel in step (d) is from about 0.05 mL to about 5 mL. Preferably, the second solution comprises an acidic solution and/or a buffer such as Tris, HEPES, MOPS and phosphate. Buffers that can be used with the present invention have a pKa in the range of from about 5.0 to about 9.0. More preferably, buffers that can be used with the present invention have a pKa in the range of from about 6.0 to about 8.0. Preferably, the second solution comprises a detergent and/or a salt. Any of the aforementioned detergents and salts can be used.

It is preferred that the second solution comprises Tris, sodium chloride and Tween 80. More particularly, the second solution comprises 0.1 M Tris (pH 7.2), 0.15 M sodium chloride and 0.5% Tween 80. The amount of this second solution that can be added to the vessel in step (d) is from about 0.05 to about 5 mL. Preferably, the amount of this second solution added to the vessel in step (d) is from about 0.5 to about 1.0 mL.

Step (e) of the above method provides for detecting the presence of *Staphylococcus aureus* in the resulting suspension in step (d). This is preferably accomplished by using a latex test such as the Slidex Staph Plus test. Preferably, 20 to 40 μL of the resulting suspension from step (d) is added to one drop of the control and then tested using a Slidex Staph Plus test. Alternatively, a Staphytect Plus test from Oxoid could be used.

The term "adsorbent" as used in the methods of the present invention is preferably selected from the group provided above, however, for the purposes of this application, the term "adsorbent" includes all adsorbent materials that neutralize, bind, and inhibit antimicrobial substances. These adsorbents include resins as defined in U.S. Pat. No. 4,632,902, and non-resinous adsorbents.

The term "resin" as used herein is a subclass of adsorbents, and is further defined to include naturally occurring and synthetic resins, for example, ion exchange resins, non-functional polymeric resin adsorbents and, in particular, polystyrene resins cross-linked with divinyl benzene.

"Non-resinous adsorbents" as used herein are another subclass of adsorbents and are defined as naturally occurring and synthetic non-resin adsorbents and molecular sieves that can be used for clarifying, deodorizing, decolorizing, and filtering. Some of these non-resinous adsorbents are the same as those used during the production of antibiotics to remove antibiotics from culture medium growing antibiotic-producing bacteria.

These non-resinous adsorbents include various forms of 1) aluminum oxide (alumina), 2) colloidal native hydrated aluminum silicates (clays), such as bentonite, kaolin, and fuller's earth, 3) crystalline hydrated alkali-aluminum silicates (sodium or calcium zeolites), 4) silica (silica gel, silica beads) such as Davisil, 5) siliceous frustules and fragments of various species of diatoms (infusorial earth, diatomaceous earth) such as Celite® (Manville Products Corporation, Denver, Colo., USA) and 6) amorphous carbon (in particular, activated carbon) such as Carboraffin, Norit® (American Norit Company Inc., Jacksonville, Fla., USA), Opocerbyl, and Ultracarbon. Naturally occurring adsorbent activated charcoal, which has been used to prevent the lethal effects of oxidation in transport media and growth media, can also be used. This media has been used for the transport of fastidious organisms such as *Neisseria gonorrhoeae* and the cultivation of *Legionella* species. Non-resinous adsorbents do not require pre-treatment with a surfactant in order to function. Treatment with surfactants may even decrease the adsorptive capabilities of these materials.

Many of these non-resinous adsorbents remove antimicrobial substances in culture. Preferred non-resinous adsorbents are the colloidal native hydrated aluminum silicates (clay) and the amorphous carbon (activated carbon) groups of adsorbent materials. Additionally preferred materials are fuller's earth or activated charcoal used singularly or in combination.

The samples used in the methods for detecting *S. aureus* according to the present invention contain media. Preferably, the media is growth media and the growth media can include general purpose media such as tryptic soy broth, brain heart infusion broth, Columbia broth and Brucella broth.

Suitable surfactants or absorption enhancers can be included in the first and second solutions as briefly described above. Other suitable surfactants or absorption enhancers that can be used in the dissociation and/or second solutions include, for example, oleic acid, polyoxyethylene derivatives of fatty acids, partial esters of sorbitol anhydride, such as for example, Tween 20, polyoxyl 40 stearate, polyoxyethylene 50 stearate, fusieates, bile salts, octoxynol and combinations thereof. Suitable surfactants include nonionic, anionic and cationic surfactants.

The present invention is further detailed in the following Example which is offered by way of illustration and is not intended to limit the invention in any manner. Standard techniques well known in the art or the techniques specifically described below are utilized.

EXAMPLE

Plastic BacT/ALERT SA culture bottles (bioMerieux, Inc.) were inoculated with 10 mL of normal human blood and one of thirty-three (33) staphylococcal isolates (17 *S. aureus*, 16 others which are non-*S. aureus* isolates). Test strains were identified using a VITEK 2 instrument (bioMerieux, Inc.) and a tube coagulase assay. Broth samples from positive bottles were mixed with an equal volume of a first solution (Solution A) and centrifuged to pellet microorganisms. The pellet was resuspended in a small volume of a second solution (Solution B) and tested with the Slidex Staph Plus latex reagents. Broth samples (10 and 100 μL) were also tested using the tube coagulase assay. A more detailed description of the method is as follows:

1. Add 5 mL of a sample from a positive BacT/ALERT SA bottle to 5 mL of Solution A in a conical tube.
2. Mix the tube contents and centrifuge for 10 min at ≧1,000G to pellet the microorganisms.
3. Remove all of the supernatant.
4. Thoroughly resuspend the pellet in 0.5-1.0 mL of Solution B by vortexing the tube.
5. Add 20-40 μL of the resulting bacterial suspension to 1 drop of the control and test using Slidex Staph Plus latex reagents (or other commercially-available kit, e.g., Staphytect Plus from Oxoid).
6. Read latex reaction according to the manufacturer's instructions.

Solution A included 0.2N NaOH, 1.0% Triton X-100 and 1 mM EDTA and Solution B included 0.1M Tris pH 7.2, 0.15M NaCl and 0.5% Tween 80. Other highly basic compounds such as ethanolamine, potassium hydroxide and tri-sodium phosphate can be substituted for sodium hydroxide.

The results of this experiment are shown below in TABLE 1. In particular, TABLE 1 shows the results of direct testing of positive SA blood cultures with the Slidex Staph Plus Latex assay. The latex reactions were graded with a reactivity of 1+ to 4+ as described in the manufacturer's instructions.

Suspensions were also prepared from a few strains of *S. aureus* and *S. epidermidis* using a two-step centrifugation procedure and a four-step centrifugation procedure. For the first procedure, approximately 7 mL of broth was centrifuged, the upper portion was then removed, saline was added and the broth was centrifuged again and resuspended in a small amount of saline. The second procedure involved preparing the pellet with saline followed by two distilled water washes with the final pellet resuspended in saline. Broth pellets from each centrifugation procedure were tested with Slidex Staph Plus latex reagents. TABLE 2 shows the results of a direct comparison of a novel method of the present invention with the 2-step and 4-step centrifugation procedures.

TABLE 1

| Strain Designation | Vitek 2 ID (3 hr test) | Tube Coagulase on colony | | Tube Coagulase on 100 ul broth | | Tube Coagulase on 10 ul broth | | Detection Time in BTA[a] | [b]Slidex Staph Plus on broth pellet |
|---|---|---|---|---|---|---|---|---|---|
| | | 4 hr at 37 C. | 24 hr at 37 C. | 4 hr at 37 C. | 24 hr at 37 C. | 4 hr at 37 C. | 24 hr at 37 C. | | |
| ATCC 43300 | S. aureus | 4 | 4 | 4 | 4 | 4 | 4 | 11.7 | 4 |
| ATCC 25923 | S. aureus | 4 | 4 | 0 | 4 | 4 | 4 | 11.7 | 2 |
| ATCC 12600 | S. aureus | 3 | 4 | 0 | 3 | 4 | 4 | 11.3 | 3 |
| ATCC 29213 | S. aureus | 4 | 4 | 3 | 3 | 4 | 4 | 10.7 | 4 |
| ATCC 6538 | S. aureus | 4 | 4 | 4 | 4 | 4 | 4 | 12.0 | 2 |
| OTC 80 | S. aureus | 4 | 4 | 4 | 4 | 4 | 4 | 11.5 | 4 |
| UCLA 114 | S. aureus | 4 | 4 | 0 | 3 | 4 | 4 | 10.8 | 3 |
| UCLA 120 | S. aureus | 3 | 4 | 0 | 0 | 1 | 3 | 12.0 | 4 |
| UCLA 121 | S. aureus | 2 | 4 | 0 | 0 | 3 | 3 | 11.8 | 3 |
| Duke 5 | S. aureus | 3 | 4 | 4 | 4 | 4 | 4 | 11.5 | 4 |
| BJ0242 | S. aureus | 4 | 4 | 3 | 4 | 4 | 4 | 12.7 | 3 |
| BJ0159 | S. aureus | 4 | 4 | 4 | 4 | 4 | 4 | 12.7 | 3 |
| D14790 | S. aureus | 4 | 4 | 4 | 4 | 4 | 4 | 11.3 | 2 |
| D14906 | S. aureus | 3 | 4 | 4 | 4 | 4 | 4 | 12.7 | 4 |
| D14908 | S. aureus | 4 | 4 | 4 | 4 | 4 | 4 | 11.8 | 2 |
| D14914 | S. aureus | 4 | 4 | 4 | 4 | 4 | 4 | 12.5 | 4 |
| D15077 | S. aureus | 4 | 4 | 0 | 4 | 4 | 4 | 12.5 | 3 |
| | % Sensitivity = | 100% | 100% | 70.6% | 88.2% | 100% | 100% | | 100% |
| ATCC 12228 | S. epidermidis | neg | neg | neg | neg | neg | neg | 16.0 | neg |
| ATCC 14990 | S. epidermidis | neg | neg | neg | neg | neg | neg | 16.7 | neg |
| ATCC 49134 | S. epidermidis | neg | neg | neg | neg | neg | neg | 16.2 | neg |
| ATCC 29997 | S. epidermidis | neg | neg | neg | neg | neg | neg | 16.2 | neg |
| 71701B | S. epidermidis | neg | neg | neg | neg | neg | neg | 15.8 | neg |
| 72401B | S. epidermidis | neg | neg | neg | neg | neg | neg | 17.0 | neg |
| 7BE4727 | S. epidermidis | neg | neg | neg | neg | neg | neg | 15.8 | neg |
| 72701B | S. epidermidis | neg | neg | neg | neg | neg | neg | 16.2 | neg |
| 72201B | S. epidermidis | neg | neg | neg | neg | neg | neg | 21.2 | neg |
| 72001B | S. epidermidis | neg | neg | neg | neg | neg | neg | 19.2 | neg |
| 72501B | S. epidermidis | neg | neg | neg | neg | neg | neg | 15.8 | neg |
| 72601B | S. epidermidis | neg | neg | neg | neg | neg | neg | 15.8 | neg |
| 7BH6481 | S. capitis | neg | neg | neg | neg | neg | neg | 14.2 | neg |
| 7BV9227 | S. warneri | neg | neg | neg | neg | neg | neg | 15.8 | neg |
| 73001B | [c]S. chromogenes | neg | neg | neg | neg | neg | neg | 17.7 | neg |
| # 155 | [d]S. saprophyticus | neg | neg | neg | neg | neg | neg | 20.2 | neg |
| | % Specificity = | 100% | 100% | 100% | 100% | 100% | 100% | | 100% |

[a]BacT/Alert
[b]100% sensitivity and specificity in 15 minutes, with proprietry buffer pretreatment.
[c]weak ID, repeat was inconclusive
[d]low discrimination ID (S. saprophyticus or S. simulans)

TABLE 2

| Strain Designation | Vitek 2 ID | New procedure | | Traditional differential centrifugation | |
|---|---|---|---|---|---|
| | | Detection Time in BTA | Latex result Buffer A/B | Latex result 2-step | Latex result 4-step |
| ATCC 25923 | S. aureus | 12.8 | 2+ | neg | neg |
| ATCC 12600 | S. aureus | 11.5 | 4+ | neg | neg |
| ATCC 29213 | S. aureus | 11.7 | 3+ | neg | neg |
| D14906 | S. aureus | 13.7 | 3+ | neg | neg |
| D15077 | S. aureus | 13.8 | 1.5+ | neg | neg |
| | Average = | 12.7 | 2.7+ | neg | neg |
| ATCC 12228 | S. epidermidis | 16.8 | neg | neg | neg |
| ATCC 14990 | S. epidermidis | 16.5 | neg | neg | neg |
| ATCC 49134 | S. epidermidis | 18.8 | neg | neg | neg |
| 71701B | S. epidermidis | 17.7 | neg | neg | neg |
| 72501B | S. epidermidis | 16.3 | neg | neg | neg |
| | Average = | 17.2 | neg | neg | neg |

As is apparent from TABLES 1 and 2, positive S. aureus latex reactions were visible on all S. aureus suspensions prepared using the described solutions, but all non-S. aureus strains tested were non-reactive resulting in 100% sensitivity and specificity. Latex results were available in approximately 15 minutes. S. aureus suspensions prepared using the traditional differential centrifugation procedure were negative. The latex results were in complete accordance with the tube coagulase and VITEK 2 results.

The method described and used in this experiment provides a rapid and 10 inexpensive method for the processing of positive standard BacT/ALERT blood culture bottles with solutions dramatically improving the sensitivity of a rapid *S. aureus* latex test. The described method allows *S. aureus* confirmation within 15 minutes of obtaining the gram stain result from a positive BacT/ALERT blood culture bottle and provide direction for susceptibility testing and subsequently aid in the recovery of the patient.

Thus, while there have been described what are presently believed to be the preferred embodiments of the present invention, those skilled in the art will realize that other and further embodiments can be made without departing from the spirit and scope of the invention, and it is intended to include all such further modifications and changes as come within the true scope of the invention.

What is claimed is:

1. A method for detecting *Staphylococcus aureus* in a sample, comprising the steps of:
    (a) mixing a sample comprising a medium and microorganisms with a first solution in a vessel, said microorganisms suspected of comprising *Staphylococcus aureus*;
    (b) separating said microorganisms from said medium and a bulk of said first solution and removing said medium and the bulk of said first solution from said vessel;
    (c) adding a second solution to said vessel to resuspend said microorganisms; and
    (d) detecting *Staphylococcus aureus* in the resulting suspension of step (c) by using an agglutination test;
    wherein said first solution comprises sodium hydroxide, polyethylene glycol tert-octylphenyl ether and EDTA, and said second solution comprises Tris, sodium chloride and polyoxyethylenesorbitan monooleate.

2. The method according to claim 1, wherein from about 0.1 to about 10 mL of said sample is mixed with said first solution in step (a).

3. The method according to claim 1, wherein from about 0.1 to about 10 mL of said first solution is mixed with said sample in step (a).

4. The method according to claim 1, wherein from about 0.5 to about 5 mL of said second solution is added to said vessel in step (c).

5. The method according to claim 1, wherein plasma, serum, blood or a blood component is mixed with said sample and said first solution in step (a).

6. The method according to claim 1, wherein said agglutination test is a latex test.

7. A method for detecting *Staphylococcus aureus* in a sample, comprising the steps of:
    (a) preparing a sample comprising a medium, microorganisms and plasma, serum, blood or a blood component, said microorganisms suspected of comprising *Staphylococcus aureus*;
    (b) mixing said sample with a first solution in a vessel;
    (c) separating said microorganisms from said medium, a bulk of said first solution and a bulk of said plasma, serum, blood or blood component and removing said medium, the bulk of said first solution and the bulk of said plasma, serum, blood or blood component from said vessel;
    (d) adding a second solution to said vessel to resuspend said microorganisms; and
    (e) detecting the presence of *Staphylococcus aureus* in the resulting suspension of step (d) by using an agglutination test;
    wherein said first solution comprises sodium hydroxide, polyethylene glycol tert-octyiphenyl ether and EDTA, and said second solution comprises Tris, sodium chloride and polyoxyethylenesorbitan monooleate.

8. The method according to claim 7, wherein from 0.1 to about 10 mL of said sample is mixed with said first solution in step (b).

9. The method according to claim 7, wherein from about 0.1 to about 10 mL of said first solution is mixed with said sample in step (b).

10. The method according to claim 7, wherein from about 0.05 to about 5 mL of said second solution is added to said sample in step (d).

11. The method according to claim 7, wherein said agglutination test is a latex test.

12. A method for detecting *Staphylococcus aureus* in a sample, comprising the steps of:
    (a) preparing a sample comprising a medium and microorganisms, said microorganisms suspected of comprising *Staphylococcus aureus*;
    (b) mixing said sample with a first solution in a vessel;
    (c) separating said microorganisms from said medium, a bulk of said first solution and removing said medium and the bulk of said first solution from said vessel;
    (d) adding a second solution to said vessel to resuspend said microorganisms; and
    (e) detecting the presence of *Staphylococcus aureus* in the resulting suspension of step (d) by using an agglutination test;
    wherein said first solution comprises sodium hydroxide, polyethylene glycol tert-octylphenyl ether and EDTA, and said second solution comprises Tris, sodium chloride and polyoxyethylenesorbitan monooleate.

13. The method according to claim 12, wherein plasma, serum, blood or a blood component is added to said sample in step (a) and separated and removed from said vessel in step (c) along with said medium and the bulk of said first solution.

* * * * *